United States Patent

Daily

[11] Patent Number: 5,522,826
[45] Date of Patent: *Jun. 4, 1996

[54] THROMBOENDARTERECTOMY DISSECTOR AND SUCTION INSTRUMENT

[76] Inventor: Pat O. Daily, 16560 El Camino Real, Rancho Santa Fe, Calif. 92067

[*] Notice: The term of this patent shall not extend beyond the expiration date of Pat. No. 5,358,507.

[21] Appl. No.: 327,706

[22] Filed: Oct. 24, 1994

Related U.S. Application Data

[63] Continuation of Ser. No. 990,908, Dec. 15, 1992, Pat. No. 5,358,507, which is a continuation-in-part of Ser. No. 736,404, Jul. 26, 1991, abandoned.

[51] Int. Cl.⁶ .................................................. A61B 19/00
[52] U.S. Cl. .......................... 606/159; 604/902; 606/190
[58] Field of Search ................................ 604/19, 22, 27, 604/35, 48, 49, 52, 53, 118, 119, 164, 264, 902, 170, 266, 267; 606/1, 159, 170, 171, 190, 194; 432/91; 128/662.06, 752, 20

[56] References Cited

U.S. PATENT DOCUMENTS

| | | | |
|---|---|---|---|
| 3,481,338 | 12/1969 | Sobel et al. | 606/190 |
| 3,963,028 | 6/1976 | Cooley et al. | 604/902 |
| 4,002,170 | 1/1977 | Hansen et al. | 604/902 |
| 4,400,168 | 8/1983 | Buechel et al. | 604/48 |
| 4,767,404 | 8/1988 | Renton | 604/268 |
| 5,197,485 | 3/1993 | Grooters | 606/159 |
| 5,358,507 | 10/1994 | Daily | 606/190 |

*Primary Examiner*—Michael H. Thaler
*Assistant Examiner*—Glenn Dawson
*Attorney, Agent, or Firm*—Baker, Maxham, Jester & Meador

[57] ABSTRACT

A suction dissector for performing coronary, systemic or pulmonary thromboendarterectomy includes a unitary elongated instrument having an elongated tubular handle section and an elongated tubular probe section having a bore. The handle section has a connector at an outer end thereof for attachment to a source of vacuum. The probe section has a rounded tip and a plurality of ports in the tip for communicating with the bore. The probe section may angled relative to the handle.

14 Claims, 1 Drawing Sheet

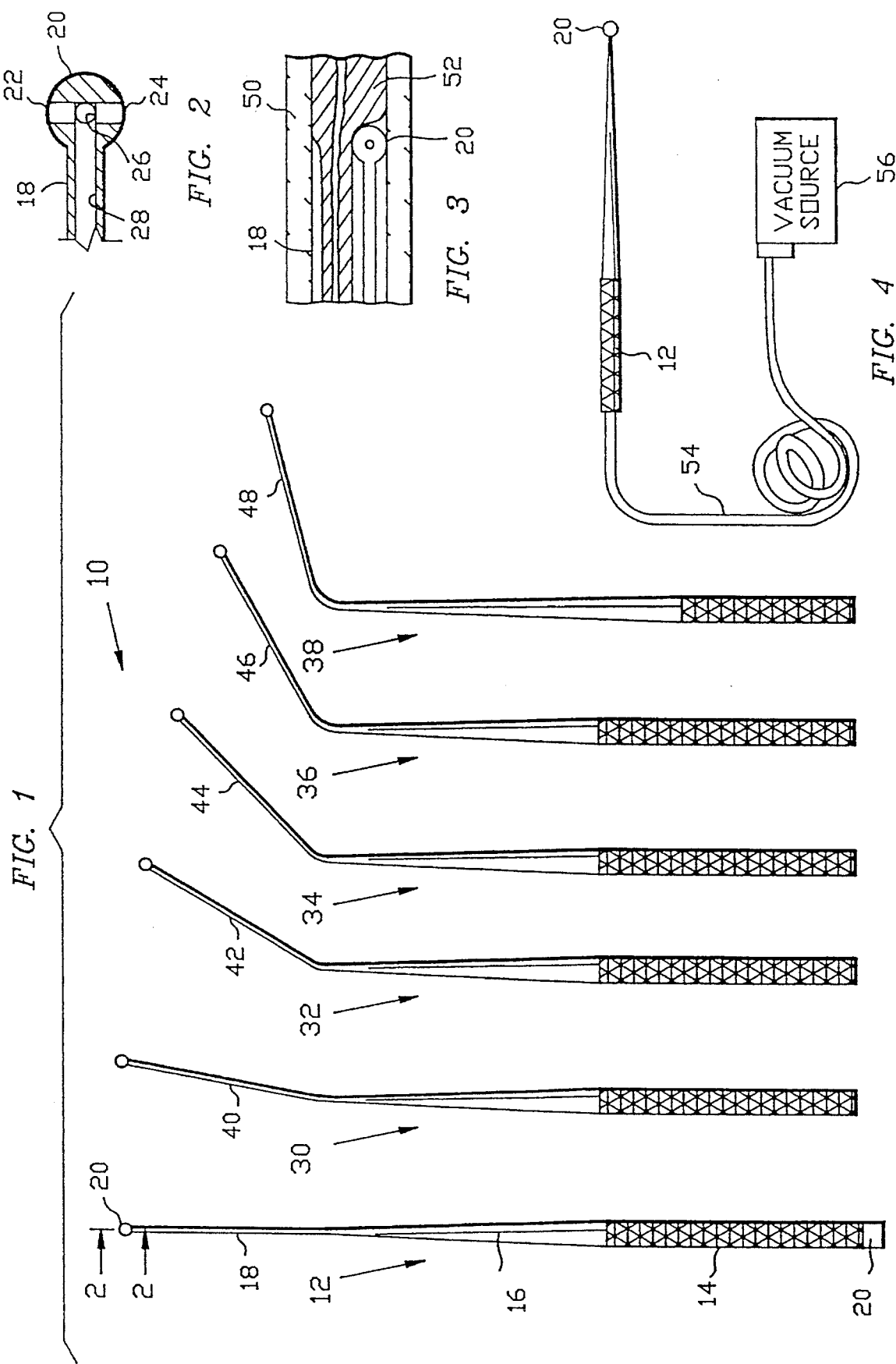

THROMBOENDARTERECTOMY DISSECTOR AND SUCTION INSTRUMENT

REFERENCE TO RELATED APPLICATION

This application is a continuation of application No. 07/990,908, filed Dec. 15, 1992 (now U.S. Pat. No. 5,358,507 granted Oct. 25, 1994, which is a Continuation-In-Part of Application Ser. No. 07/736,404, filed Jul. 26, 1991, now abandoned, and entitled "Cardiac Thromboendarterectomy Suction Dissector".

BACKGROUND OF THE INVENTION

The present invention relates to surgical instruments and procedures and pertains particularly to improved thromboendarterectomy instruments and method of use.

Many cardiovascular diseases involve arteriosclerosis or clogged systemic and pulmonary arteries. Many heart and circulatory problems are due to clogged or restricted arteries. Arteries become clogged due to plaque buildup on the walls of the arteries as well as clot formation and/or embolization. Surgical techniques have been developed in the past for cleaning out or unplugging many of these arteries.

These techniques involve the use of special surgical instruments in the form of various shaped scrapers that are inserted in the artery to separate and dislodge the plaque material from the arterial walls. Various implements have been proposed and utilized for this procedure in the past. Most of these instruments are referred to as dissectors and resemble tiny spoons or spatulas on the end of a long slim rod.

Pulmonary thromboendaractomary also normally involves frequent periods of circulatory arrest. Even during circulatory arrest, continued back bleeding obscures the operative field. This requires frequent interruption of the procedure to allow aspiration of the operative field with a second instrument. These interruptions obviously extend the periods of circulatory arrest, sometimes to the detriment of the patient.

It is, therefore, desirable that improved implements and procedures be available which effectively remove plaque and the like from arteries and provide aspiration to remove blood at the same time.

SUMMARY AND OBJECTS OF THE INVENTION

It is the primary object of the present invention to provide an improved instrument for the removal or separation of plaque, clot and the like from artery walls.

It is another object of the present invention to provide an improved method for the removal or separation of plaque and the like from artery walls.

In accordance with a primary aspect of the present invention, an improved endarterectomy instrument includes an elongated tubular instrument having means for connection to a suction source and having a spherical tip for insertion into an artery for dissection and removal of plaque and the like.

Another aspect of the invention includes an improved endarterectomy instrument set having a plurality of elongated tubular instruments having means for connection to a suction source, and each having an elongated probe extending at a different angle to the handle, with a spherical tip for insertion into an artery for removal of plaque and the like.

A further aspect of the invention comprises an improved endarterectomy procedure using an instrument set having a plurality of elongated tubular instruments having means for connection to a suction source, and each having an elongated probe extending at a different angle to the handle with a spherical tip for insertion into an artery for the simultaneous aspiration of fluids and removal of plaque and the like.

BRIEF DESCRIPTION OF THE DRAWING

The above and other objects and advantages of the present invention will become apparent from the following description when read in conjunction with the accompanying drawings wherein:

FIG. 1 is a top plan view illustrating a set of instruments in accordance with the preferred embodiment of the present invention;

FIG. 2 is an enlarged detailed section view showing details of construction of a tip of an instrument in accordance with the invention;

FIG. 3 is a side elevation view in section showing an instrument in accordance with the invention in use; and FIG. 4 is a schematic illustration of a system incorporating an instrument of the invention.

DETAILED DESCRIPTION OF A PREFERRED EMBODIMENT

Referring to FIG. 1 of the drawings, a set of instruments in accordance with the invention is illustrated and designated generally by the numeral 10. The instruments, as will be appreciated, are similar in construction, with each having an elongated probe tip that extends at a different angle to the handle. These instruments are referred to as endarterectomy dissectors.

Referring to FIG. 1, there is illustrated a kit comprising a plurality of instruments comprising a first dissector 12 of a hollow or tubular configuration having a handle section 14 for grasping, with an elongated converging section 16 extending downward to an elongated probe section 18 having a small diameter and a larger rounded or spherical tip 20. The tip may have substantially any configuration, but the enlarged spherical configuration is preferred. The handle 14 has a port at an end 22 for attachment to a vacuum source and cell saving device. The probe section of the instrument 12 is aligned with and coaxial of the handle 14. The probe section has a diameter preferably on the order of about 1.5 millimeters, and a tip 20 which is preferably generally spherical in configuration and having a diameter of on the order of about two (2) millimeters. This tip is designed to act as a blunt dissector by engaging and forcing plaque and the like away from artery walls.

Referring to FIG. 2, the tip 18 is provided with a pair of cross bores extending at ninety degree angles therethrough defining a plurality of suction ports 24, 26 disposed around the periphery of the tip or head 20 and communicating by way of the internal bores, with an internal passage 28 of the probe. This instrument has been found to be effective when connected to a vacuum source and inserted into an artery to strip away plaque or clot therein, while at the same time removing blood and other fluids. These dissectors perform the combined function of blunt dissection and aspiration. They continually remove blood and other fluids as well as plaque and/or clot particles from the artery as they are being manipulated therein. This eliminates the need for stopping the dissection repeatedly and to aspirate blood from the operative field with a second instrument.

The instrument set or system comprises a plurality of the instruments 12, 30, 32, 34, 36 and 38. The main difference between the instruments is in the length and angle of the probe tip section with respect to the handle. The probe lengths vary from about three to about seven centimeters (cm). The angle varies from zero up to just short of ninety degrees. The angle and tip lengths of the dissector tips facilitate dissection of all of the bronchopulmonary segmental arteries of the lungs as well as those of the heart and rest of the body.

The instrument 30 is shown with a tip 40 having an angle of on the order of about fifteen degrees to the axis of the handle. This angle may vary some from this, but on the order of about this angle is desired for certain operations. The distance from the angle to the tip is about five (5) centimeters.

The instrument 32 is illustrated as having a probe tip 42 that is on the order of about thirty degrees from the angle of the axis of the handle. This angle may vary slightly as desired. The length from the angle to the tip is about five (5) centimeters.

The instrument 34 is illustrated having a tip 44 on the order of about forty-five degrees to the axis of the handle. Again, this angle may vary slightly, depending on various factors. The length of the probe from the angle to the tip is about five (5) centimeters.

The instrument 36 is illustrated having a probe tip 46 of on the order of about sixty degrees from the axis of the handle. The length of the probe from the angle or bend to the tip is about five (5) centimeters. These dissectors, as will be appreciated, enable the surgeon to select the instrument having the tip at the proper or desired angle for the particular situation encountered.

The instrument 38 is shown to have a probe tip 48 on an angle just short of ninety degrees or on the order of about eighty to eighty-five degrees to the axis of the handle. This, of course, may extend up to ninety degrees, if desired. The length of the probe from the angle to the tip is on the order of about three (3) centimeters.

It will also be appreciated from viewing the instruments in FIG. 1 that the straight section of the probe tip may vary in length from its full length at the juncture of the transition section down to shorter section, as will be appreciated. The instrument 12, for example, preferably has a section that is on the order of approximately seven centimeters in length, with others having an angled straight portion being on the order of about five centimeters in length, with instruments 38 being on the order of about three centimeters in length. The tip is preferably on the order of about two millimeters in diameter, with the ports 24, 26 being on the order of about 0.5 millimeters in diameter.

Referring to FIG. 3, there is illustrated an example with instrument 12 in use, with the probe section 18 extending into the bore of an artery 50 and stripping plaque 52 away from the wall of the artery. The probe 18 with its tip 20 is shown to have forced a portion of the plaque away from surface of the wall. The instrument draws blood and other fluids into the ports from all directions around it while plaque or like material is being removed.

Referring to FIG. 4, a dissector 12 is shown connected by means of a standard suction tubing 54 to a suction unit or vacuum source 56. It may be connected to any suitable vacuum source, such as a wall suction, a Cell Saver device, or cardiotomy suction to conserve blood. Blood, plaque and other debris drawn in via the dissector may be collected in a screen or the like for disposal. The instruments are preferably constructed of stainless steel and fitted in a stainless steel sterilizing case. However, the instruments may be constructed of a suitable plastic material and be disposable.

In operation, an instrument having the appropriate angle probe tip is selected, the instrument is connected by a flexible tubing to a source of vacuum, such as a vacuum pump. Access to an artery is obtained and the instrument is inserted in the correct plane along the artery, probing therein simultaneously aspirating blood and other debris from the interior of the artery while separating plaque, clot and the like from the wall of the artery. The tip of the instrument is probed along the wall and through an occluded area of the artery forcing all plaque away from the wall. The plaque may be grasped by tweezers or a like instrument and pulled from the artery as it is stripped from the walls thereof.

While I have illustrated and described my invention by means of specific embodiments, it should be understood that numerous changes and modifications may be made therein without departing from the spirit and scope of the invention as defined in the appended claims. I further assert and sincerely believe that the above specification together with the accompanying drawings contains a written description of the invention and the manner and process of making and using it, in such full, clear, concise, and exact terms as to enable any person skilled in the art to which it pertains, or with which it is most nearly concerned, to make and use the same, and further that it sets forth the best mode contemplated by me for carrying out the invention.

I claim:

1. A combination dissector and suction instrument for performing pulmonary thromboendarterectomy, said instrument comprising:

a unitary elongated tubular member, said member having a handle section on one end thereof and having means for connection to a source of vacuum, an elongated substantially rigid probe section adapted for insertion in and extension along an artery, said probe section having an unobstructed uniform cylindrical outer surface of from three to seven cm in length and 1.5 mm in diameter with a rounded tip of about 2 mm in diameter having a plurality of suction inlet ports and, said probe section extending at an angle to said handle section of between from about zero to about eighty degrees.

2. An instrument according to claim 1 wherein said ports are circular and about 0.5 mm in diameter and disposed at about ninety degree intervals about said tip.

3. An instrument according to claim 1 wherein said probe section is about 3 cm in length and at about an eighty degree angle to said handle.

4. A combination dissector and suction instrument instrument for performing thromboend-arterectomy, comprising:

a unitary elongated tubular member, said member having a handle section on one end thereof and having means for connection to a source of vacuum, an elongated substantially straight rigid probe section adapted for insertion in and extension along an artery, said probe section having an unobstructed uniform cylindrical outer surface of at least three cm in length with a rounded tip having a plurality of suction inlet ports and, said member having said probe section extending relative to said handle section, a selected one of fifteen degrees, thirty degrees, forty-five degrees, sixty degrees and eighty degrees to said handle section, respectively, wherein said rounded tip is spherical and two mm in diameter and has four circular suction inlet ports of 0.5 mm in diameter.

5. An instrument according to claim 4 wherein the probe section is from about 3 cm to about 7 cm in length.

6. An instrument according to claim 5 wherein said probe section has an unobstructed uniform cylindrical outer surface.

7. An instrument according to claim 6 wherein said probe section is about 3 cm in length and at about an eighty degree angle to said handle.

8. An instrument according to claim 4 wherein said probe section has an unobstructed uniform cylindrical outer surface from about 3 cm to about 7 cm in length.

9. An instrument according to claim 8 wherein said ports are disposed at about ninety degree intervals about said tip.

10. An instrument according to claim 9 wherein said probe section is about 3 cm in length and at about an eighty degree angle to said handle.

11. An instrument according to claim 4 wherein said probe section is about 3 cm in length and at about an eighty degree angle to said handle.

12. A method of performing thromboendarterectomy, said method comprising the steps of:

selecting a combination dissector and suction instrument of unitary elongated substantially rigid structure having an elongated tubular handle section and an elongated tubular probe section having a through bore, said elongated tubular handle section having means at an outer end thereof for attachment to a source of vacuum, said elongated tubular probe section having a rounded tip and a plurality of ports in said rounded tip communicating with said bore, said combination dissector and suction instrument having said elongated tubular probe section extending a selected one of, coaxially with said elongated tubular handle section, and at an angle to said elongated tubular handle section of between about fifteen degrees and about eighty degrees, relative to said handle section;

connecting said outer end of said combination dissector and suction instrument to a vacuum source; and inserting said elongated tubular probe section of said combination dissector and suction instrument into and moving it along an artery forcing plaque from walls thereof while simultaneously therewith operating said source of suction to maintain an area around said rounded tip substantially free of fluids.

13. A method according to claim 12 wherein said angle to said elongated tubular handle section of between about fifteen degrees and about eighty degrees, comprises a selected one of fifteen degrees, thirty degrees, forty-five degrees, sixty degrees and eighty degrees, respectively.

14. A method according to claim 12 wherein said rounded tip is two mm in diameter and said plurality of ports includes four circular vacuum ports of 0.5 mm in diameter.

* * * * *